United States Patent
Grittani et al.

(10) Patent No.: US 10,603,514 B2
(45) Date of Patent: Mar. 31, 2020

(54) DEVICE AND METHOD FOR HIGH DOSE PER PULSE RADIOTHERAPY WITH REAL TIME IMAGING

(71) Applicant: FYZIKALNI USTAV AV CR, V.V.I., Prague (CZ)

(72) Inventors: Gabriele Maria Grittani, Dolni Brezany (CZ); Tadzio Levato, Dolni Brezany (CZ); Carlo Maria Lazzarini, Dolni Brezany (CZ); Georg Korn, Dolni Brezany (CZ)

(73) Assignee: FYZIKALNI USTAV AV CR, V.V.I., Prague (CZ)

( * ) Notice: Subject to any disclaimer, the term of this patent is extended or adjusted under 35 U.S.C. 154(b) by 0 days.

(21) Appl. No.: 16/309,668

(22) PCT Filed: Jun. 9, 2017

(86) PCT No.: PCT/CZ2017/050023
§ 371 (c)(1),
(2) Date: Dec. 13, 2018

(87) PCT Pub. No.: WO2017/211331
PCT Pub. Date: Dec. 14, 2017

(65) Prior Publication Data
US 2019/0329071 A1    Oct. 31, 2019

(30) Foreign Application Priority Data
Jun. 10, 2016   (LU) .......................................... 93102

(51) Int. Cl.
*A61N 5/10*    (2006.01)
*A61N 5/06*    (2006.01)
(Continued)

(52) U.S. Cl.
CPC ............. *A61N 5/1071* (2013.01); *A61N 5/06* (2013.01); *A61N 5/1067* (2013.01);
(Continued)

(58) Field of Classification Search
CPC ................ A61N 5/1071; A61N 5/1075; A61N 5/103–1084; A61N 2005/1072; A61N 2005/1076; A61N 2005/1085–1094
See application file for complete search history.

(56) References Cited

U.S. PATENT DOCUMENTS 8,039,819 B2    10/2011  Faure et al.
9,044,604 B2     6/2015  Dirauf
(Continued)

OTHER PUBLICATIONS

Le Garrec Bruno et al., "ELI-beamlines: extreme light infrastructure science and technology with ultra-intense lasers", Optomechatronic Micro/Nano Devices and Components III : Oct. 8-10, 2007, Lausanne. Switzerland: [Proceedings of SPIE, ISSN 0277-786], SPIE, Bellingham. Wash, vol. 8962, Feb. 25, 2014 (Feb. 25, 2014(.
(Continued)

*Primary Examiner* — Thaddeus B Cox
(74) *Attorney, Agent, or Firm* — Soroker Agmon Nordam

(57) ABSTRACT

A radiotherapy system comprising at least one pulsed radiation source, at least one imaging system, a control system, and a synchronization system is disclosed. The pulsed radiation source deposits high dose radiation pulses to a target region inside the patient; simultaneously the imaging system is used to monitor the target region, synchronized by the synchronization system. The dose per radiation pulse is high enough to deposit, within few pulses, 1 Gy at a depth of at least 1 cm in water. At each irradiation time step, the pulsed radiation source delivers short pulses of radiation (<1 ms) and the imaging system performs a snapshot of the position, and eventually the shape, of the target region during the irradiation time, with a time resolution better than
(Continued)

200 ms. Being both the pulsed radiation source and imaging system synchronized by the synchronization system with less than 200 ms jitter, this system allows for very precise reconstruction of the map of the dose deposited into the target region.

20 Claims, 5 Drawing Sheets

(51) Int. Cl.
   *A61N 5/067* (2006.01)
   *G01J 11/00* (2006.01)
   *G01T 1/29* (2006.01)
(52) U.S. Cl.
   CPC .......... *A61N 5/1075* (2013.01); *A61N 5/1039* (2013.01); *A61N 2005/067* (2013.01); *A61N 2005/109* (2013.01); *A61N 2005/1088* (2013.01); *A61N 2005/1089* (2013.01); *G01J 11/00* (2013.01); *G01T 1/29* (2013.01)

(56) References Cited

U.S. PATENT DOCUMENTS

| | | | |
|---|---|---|---|
| 2006/0203967 A1* | 9/2006 | Nilsson | A61B 6/542 378/207 |
| 2012/0294423 A1 | 11/2012 | Cheung | |
| 2013/0256565 A1* | 10/2013 | Claesson | A61N 5/1049 250/492.1 |
| 2015/0124930 A1 | 5/2015 | Verhaegen | |
| 2015/0157879 A1 | 6/2015 | Wu | |
| 2016/0263402 A1* | 9/2016 | Zhang | A61N 5/1071 |
| 2017/0252579 A1* | 9/2017 | Kilby | A61N 5/1071 |

OTHER PUBLICATIONS

S. Farsiu et al., "Statistical detection and imaging of objects hidden in turbid media using ballistic photons", Applied Optics, (20070000), vol. 46, No. 23, doi:doi:10 1364/AO.46.005805, XP001506962.

* cited by examiner

[Fig. 1]
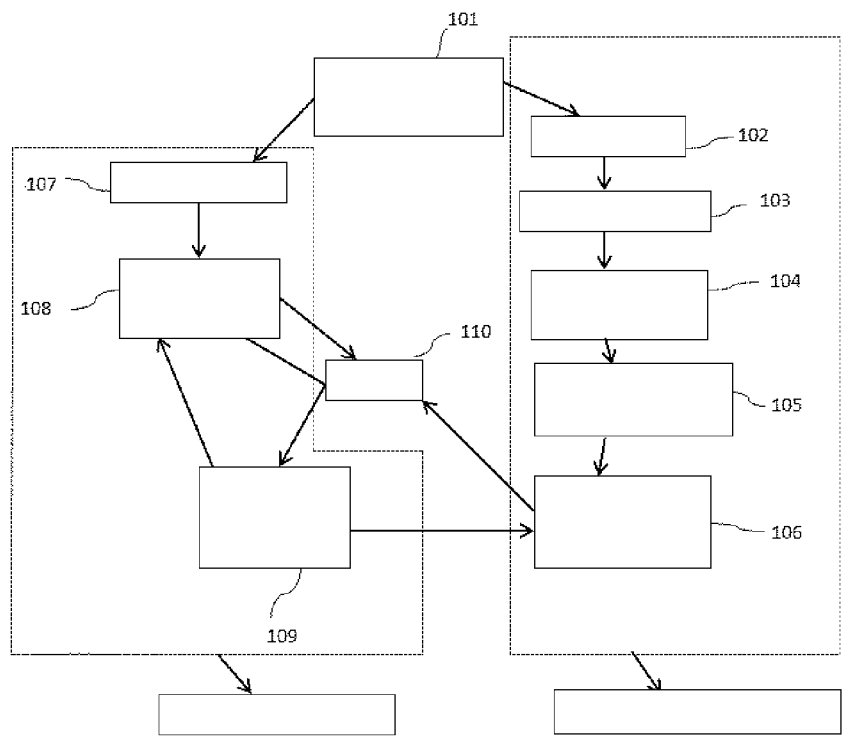
[Fig. 2]
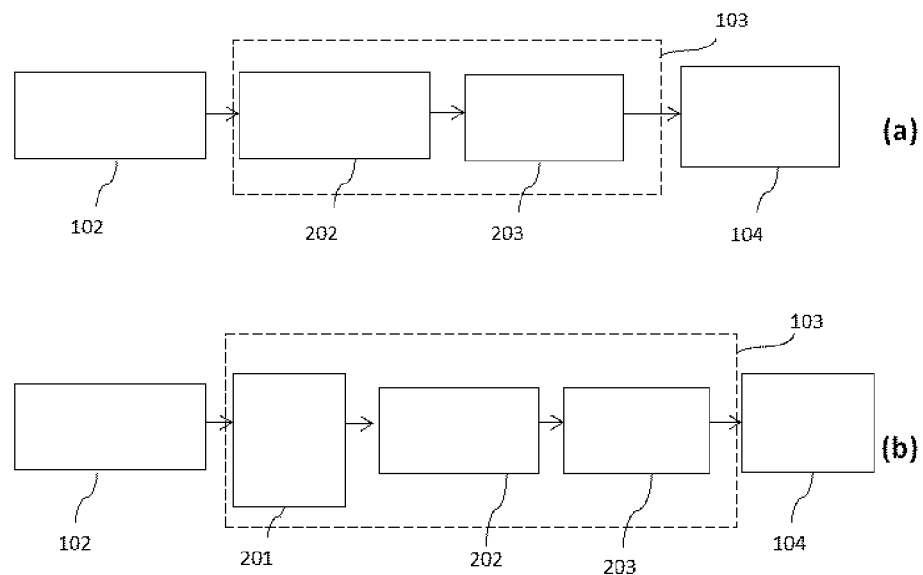

[Fig. 3]
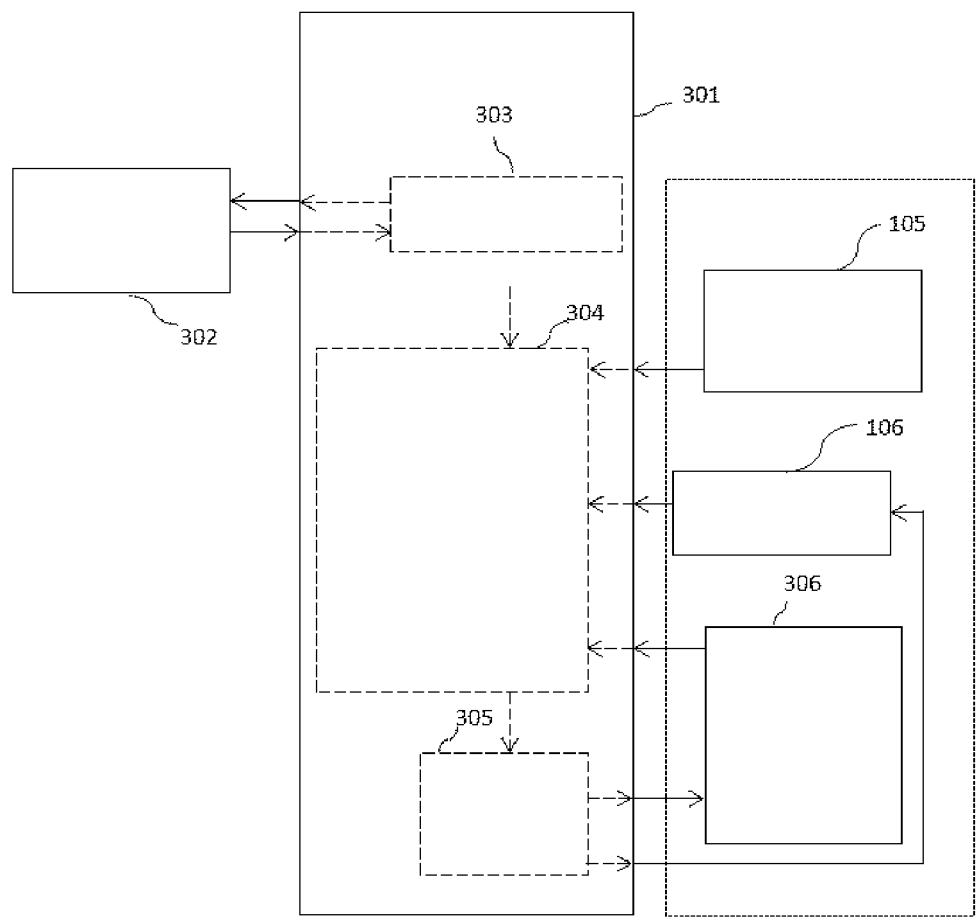

[Fig. 4]
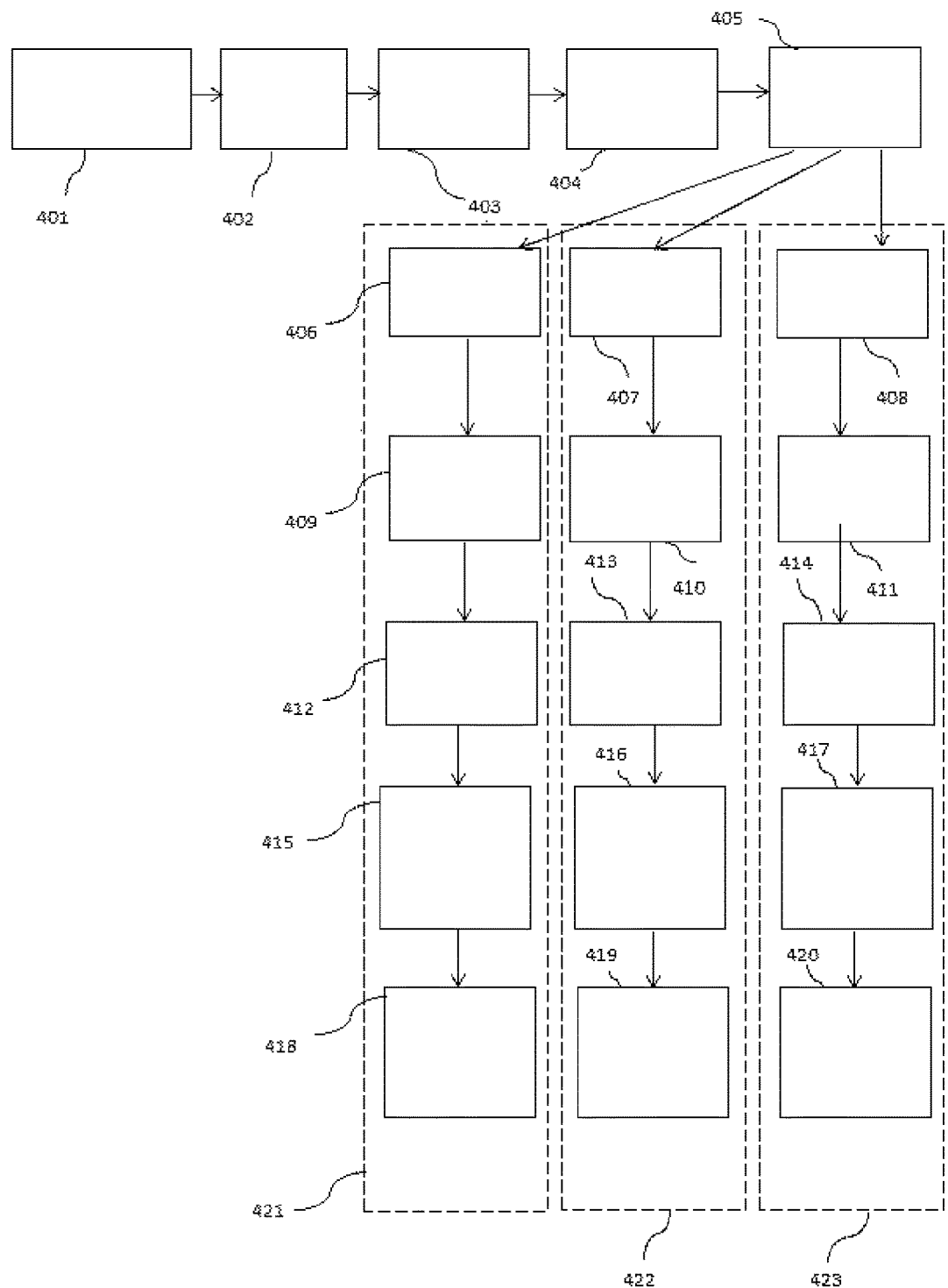

[Fig. 5]
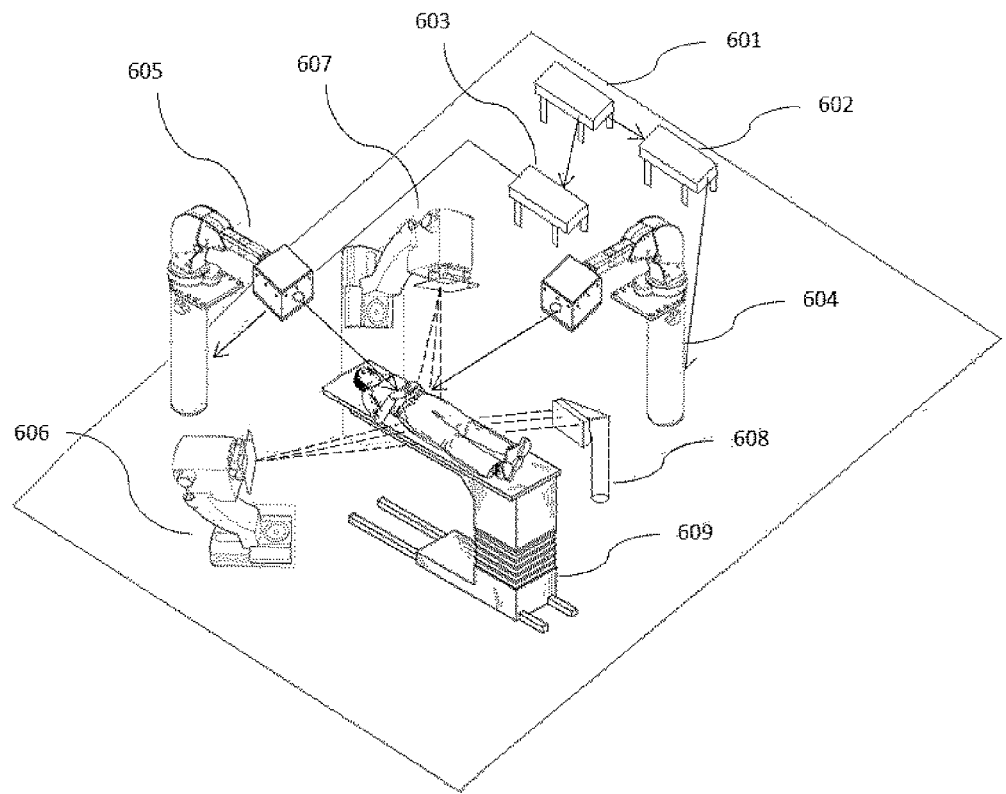
[Fig. 6]
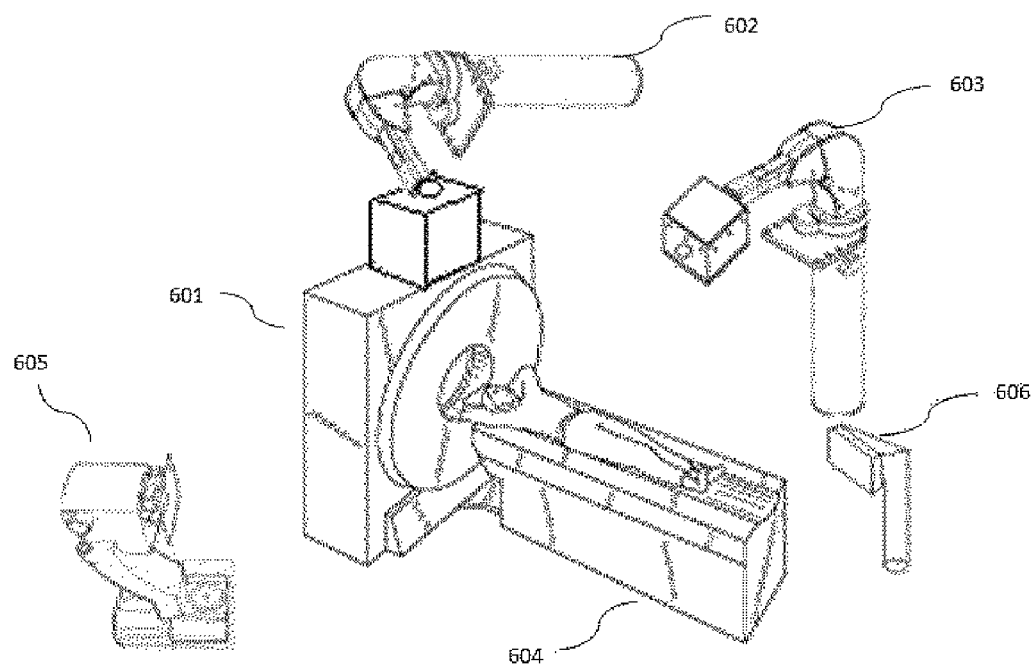

[Fig. 7]
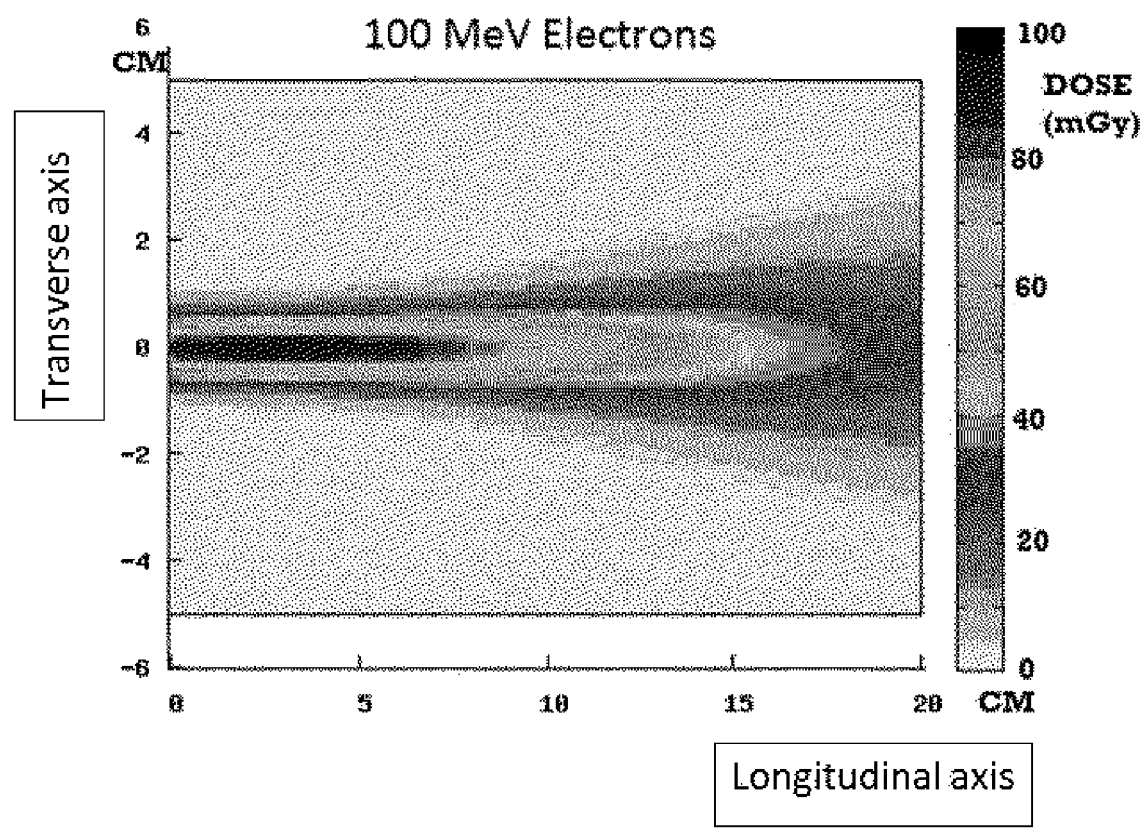

DEVICE AND METHOD FOR HIGH DOSE PER PULSE RADIOTHERAPY WITH REAL TIME IMAGING

TECHNICAL FIELD

The invention relates to a radiotherapy system which allows the monitoring of the position of the target region during the treatment and thus allowing effective radiotherapeutic treatment.

BACKGROUND ART

Radiotherapy is an important treatment for many types of cancer. This technique relies on the use of radiation sources to deliver dose to a target region within the patient's body. Furthermore, radiotherapy is not restricted only to cancer treatment, but can be applied in general to deliver dose to a target region within the patient's body as in the case, for example, of radiosurgery.

In the state of the art, radiotherapy is, in most of the cases, performed using radio frequency accelerators, which are devices capable of delivering electron or gamma beams with energy typically in the range 6-30 MeV. Due to their technology, these devices usually deliver very wide beams on the order of 10×10 cm2 and a dose rate of few Gy/min. Typically, such devices deliver to the target region 0.1-1 mGy per pulse, at a frequency of few hundreds Hz. Treatments with these devices usually last at least few minutes. During this time the target region within the patient's body can move, due, for example, to patient's breathing. For this reason huge effort is put in imaging the target region during the treatment.

U.S. Pat. No. 9,044,604 discloses a radiotherapy system including a radiotherapy module and at least one X-ray imaging module. Using radio frequency accelerators, due to the low dose per pulse and to the high number of pulses needed, it is not feasible to perform radiography at each irradiation step. One of the reasons is that each radiography delivers additional dose to the patient.

U.S. Pat. No. 8,039,819 discloses a device for creating a spatial dose distribution in a medium volume, the device comprising a laser system and at least one electron source for releasing a plurality of high-energy quasi-monoenergetic electron pulses upon irradiation with said laser pulses. The disclosed device produces ultra-short radiation pulses (<1 ms) with very high energy (>50 MeV), but it is lacking a synchronized imaging system and a feedback control that exploits the treatment effectiveness due to the shortness of the radiation pulses.

SUMMARY OF INVENTION

The present invention provides a system for radiotherapy which comprises at least one pulsed radiation source for delivering radiation pulses shorter than 1 ms, at least one imaging system, at least one control system for determining the deposited dose, and at least one synchronization system for synchronizing said pulsed radiation source and said imaging system within a time jitter shorter than 200 ms, wherein said pulsed radiation source is capable of delivering a dose of at least 50 mGy at a depth of at least 1 cm in water within a single pulse, wherein said imaging system has the time resolution better than 200 ms, and wherein said control system is connected to the pulsed radiation source and to the imaging system.

The system of the present invention, by enabling depositing in a target region of a very high dose per pulse, by imaging the target region during each irradiation time step, and by retrieving the dose deposited map after each irradiation time step, allows to achieve a very effective treatment because it allows to determine the dose deposited in the individual parts of the treated region of the body, and the position of the target region after each irradiation time step is monitored, hence allowing adapting and improving the treatment plan after any irradiation time step, whenever necessary. By delivering higher dose per pulse, it is possible to perform a patient treatment session with just few radiation pulses. Using a synchronized imaging system, it is possible to gain information about the position, and eventually the shape, of the target region during each irradiation time step. This synchronized imaging helps to understand how precisely the target region has been irradiated, and this information can be used for improving the dose delivery in the subsequent pulses. Furthermore, this imaging may be used to foresee the target region position, and eventually shape, for the following radiation pulses.

With a radiation pulse shorter than 1 ms, with the time resolution of the imaging system shorter than 200 ms, and with the time jitter between them shorter than 200 ms, the target region irradiation and imaging happens in a time window smaller than 400 ms. Said time resolution is short enough that most of the patient's body internal structure can be considered still.

In this way it is possible to image the position, and optionally the shape, of the target region, with respect, for example, to markers and/or internal organs or bones of the patient's body, within an overall time window of less than 400 ms. After processing the data from the imaging system and the pulsed radiation source, it is possible to retrieve the dose deposited distribution in the target region and, eventually, in the patient's body. This information can be used to modify, according to patient specific needs, the patient's treatment plan. For this reason the invention disclosed herein brings advantages in the direction of Personalized Medicine.

By combining the imaging data with the radiation pulse data, a map of the dose deposited into the patient's body can be reconstructed with a very high accuracy due to the fact that the patient is still during the whole irradiation and imaging process. The reconstruction of the deposited dose map can be done either after each radiation pulse, after few of them or after the whole treatment session. The advantage is that this provides a better understanding of where the dose has been really deposited into the patient's body. In particular, performing a reconstruction of the dose deposited after one or more radiation pulses, and adjusting the treatment plan according to this information after one or more pulses, can lead to an higher dose deposited into the target region and to a lower dose deposited in the surroundings of the target region, inside the patient's body. This method can be more effective than conventional methods in performing a more personalized treatment.

In a preferred embodiment, the synchronization system is an electrical device capable of sending electrical pulses synchronized with a tunable delay within a time resolution better than 200 ms.

The pulsed radiation source creates and delivers radiation beams to the patient. Each pulse of radiation is shorter than 1 ms and delivers a dose of at least 50 mGy at a depth of at least 1 cm in water.

The pulsed radiation source can preferably be selected from the group comprising sources of electron beams, sources of high energy photon beams, sources of positron beams, sources of neutron beams, sources of pi meson beams, sources of beams comprising combinations of these particles.

The pulsed radiation source can in one embodiment comprise a laser plasma electron accelerator. The electron beam emitted from the accelerator can be used as the radiation beam, or may be converted in the pulsed radiation source into a beam of high energy photons, positrons, neutrons or pi mesons, or of a mixture of these particles.

The pulsed radiation source may comprise a laser emission system, a laser transport, a laser focusing system, a plasma electron accelerator, a radiation beam delivery system. In one embodiment, the radiation beam delivery system is adapted for checking the electron beam quality and/or stopping or modifying the beam in order to achieve predetermined criteria (e.g., determined by the treatment plan). In one embodiment, the radiation beam delivery system may use the kinetic energy of the electron beam to create a different particle beam, for example a beam of high energy photons, positrons, neutrons or pi mesons.

In a preferred embodiment, the laser emission system is a Ti:Sa laser, for delivering laser pulses with energy of at least 100 mJ and pulse duration shorter than 1 µs; more particularly a Ti:Sa laser, pumped by diode pumped solid state lasers with frequency conversion, for delivering laser pulses with energy of at least 100 mJ and pulse duration shorter than 1 µs.

In a preferred embodiment, the laser transport comprises at least one system selected from: a compressor for compressing the laser pulse in time to less than 100 fs, and an optical transport line for sending the laser pulse to the laser focusing system; a compressor, an optical transport line and a phased optical fiber array for transporting an uncompressed laser pulse with time duration of at least 10 ps to the compressor, whereas the compressor is capable of compressing the laser pulse in time to less than 100 fs and then sending the laser pulse to the optical transport line for sending the laser pulse to the laser focusing system.

In a preferred embodiment, the laser focusing system may be an optical system for focusing the laser pulses into the plasma electron accelerator, comprising at least one positioning mirror and at least one off-axis parabola capable of focusing the laser pulses to intensity higher than $10^{12}$ W/cm$^2$.

In another preferred embodiment, the laser focusing system is an optical system for focusing the laser pulses into the plasma electron accelerator, comprising at least one positioning mirror and at least one spherical mirror capable of focusing the laser pulses to intensity higher than $10^{12}$ W/cm$^2$.

In a preferred embodiment, the plasma electron accelerator is a device comprising at least one gas target mounted on a remotely controlled motorized stage with at least one degree of freedom to align the gas target according to the laser focus.

In a preferred embodiment, the radiation beam delivery system comprises at least one of the following components: a magnetic field for selecting the energy of the beam and for optionally shaping the beam, a beam charge diagnostic, a magnetic system for changing the size of the beam, and optionally for focusing or defocusing it, and a solid target converter for generating other particle beams.

The pulsed radiation source may preferably comprise at least one laser beam diagnostic, selected from: a spectral shape diagnostic for measuring the spectral shape of the laser pulse; an energy diagnostic for measuring the energy of the laser pulse; a beam shape diagnostic for measuring the energy distribution of the laser pulse along its transverse section; a spectral phase diagnostic for measuring the spectral phase of the laser pulse; a temporal profile diagnostic for measuring the temporal profile of the laser pulse; a laser focal spot diagnostic for measuring the spatial distribution of the laser pulse in its focus; and a wavefront diagnostic for measuring the phase front of the laser pulse.

In a preferred embodiment, the spectral shape diagnostic can be an optical and/or infrared light spectrometer.

Preferably, the energy diagnostic comprises a calorimeter; and/or at least one optical diode.

In a preferred embodiment, the beam shape diagnostics comprises a set of mask filters; and/or a camera and imaging optics.

In a preferred embodiment, the spectral phase diagnostic comprises at least one of the following devices: SPIDER, FROG, D-SCAN and GRENOUILLE.

In a preferred embodiment, the temporal profile diagnostic comprises at least one of the following devices: SPIDER, FROG, D-SCAN and GRENOUILLE.

In a preferred embodiment, the electron beam shape diagnostic comprises a fluorescent screen coupled with a CCD.

In a preferred embodiment of the device, the electron beam charge diagnostic comprises at least one Integrating Current Transformer and/or at least one fluorescent screen coupled with a CCD.

In a preferred embodiment, the electron beam spectral shape diagnostic comprises a magnetic dipole and a fluorescent screen coupled with a CCD.

In a preferred embodiment, the laser focal spot diagnostic comprises a CCD and a reflective object.

In a preferred embodiment, the wavefront diagnostic comprises a wavefront sensor.

The pulsed radiation source may further comprise a gas target for emitting the electron pulses, which can optionally be monitored by one or more diagnostics selected from a plasma diagnostic for measuring the plasma density inside the target; a laser plasma coupling diagnostic for measuring the coupling in the laser plasma interaction; and a laser propagation diagnostic for measuring the laser propagation after the plasma.

The electron pulses accelerated by the plasma electron accelerator can preferably be monitored by one or more diagnostics selected from an electron beam shape diagnostic for measuring the transverse shape of the electron pulse; a beam charge diagnostic for measuring the charge of the electron pulse; an electron beam spectral shape diagnostic for measuring the spectral shape of the electron pulse; a beam divergence diagnostic for measuring the divergence of the electron pulse; and a beam temporal profile diagnostic for measuring the temporal profile of the electron pulse.

In a preferred embodiment, the plasma diagnostic comprises at least one CCD with imaging optics looking at the gas target.

In a preferred embodiment, the laser propagation diagnostic comprises a CCD looking at the laser exiting the target.

In a preferred embodiment, the laser plasma coupling diagnostic comprises a CCD with imaging optics looking at the light emitted by the target.

In a preferred embodiment, the beam divergence diagnostic comprises a fluorescent screen coupled with a CCD.

In a preferred embodiment, the beam temporal profile diagnostic comprises a streak camera with a resolution better than 10 ps.

In another embodiment, the beam temporal profile diagnostic comprises an infrared spectrometer and a solid target.

The pulsed radiation source may further comprise a control system for the electron beam optimization for collecting the data from all diagnostics, analyzing said data and optionally saving the results. If the electron beam does not satisfy the parameters required for the treatment, the control system for the electron beam optimization modifies the position or state of the pulsed radiation source components until the electron beam reaches the parameters desired.

The pulsed radiation source may preferably comprise at least one of the following components: a spectral shaping device for modifying the spectral shape of the laser pulses; an energy attenuator for changing the energy of the laser pulses; a spectral phase shaper for modifying the spectral phase of the laser pulses; compressor gratings motors for changing the temporal profile of the laser pulses; positioning motors for modifying the path of the laser pulses in the laser focusing system; focusing optics motors for modifying the position and the shape of the laser focal spot; a gas density shaper for modifying the density profile of the gas target; gas target motors for changing the position of the gas target within the plasma electron accelerator; adaptive optics for modifying the wavefront of the laser pulse and so also the shape of the focal spot; a radiation spectrum fine shaper for modifying the spectrum of the radiation pulse; a radiation pulse particle number controller for adjusting the number of particles in the radiation pulse; a radiation pulse spatial distribution shaper for modifying the spatial distribution of the radiation pulse; a radiation pulse divergence controller for adjusting the divergence of the radiation pulse; and a radiation pulse temporal profile controller for adjusting the temporal profile of the radiation pulse. The control system for the electron beam optimization is adapted to operate on at least one of these pulsed radiation source components and/or it is connected to at least one of these pulsed radiation source components.

In a preferred embodiment, the spectral shaping device is a mazzler.

Preferably, the spectral shaping device comprises at least one colored optical filter; and/or at least one prism and at least one neutral optical filter.

In a preferred embodiment, the energy attenuator comprises at least one half-lambda plate and at least one polarizer.

In a preferred embodiment, the spectral phase shaper is a dazzler.

In a preferred embodiment, the adaptive optics comprises a deformable mirror.

In a preferred embodiment, the compressor gratings motors are at least one linear stage mounted below one of the gratings to change the optical path of the different wavelengths.

In a preferred embodiment, the positioning motors are at least one actuator mounted on at least one mirror mount capable of moving with at least one degree of freedom the at least one positioning mirror.

In a preferred embodiment, the focusing optics motors comprise at most five rotation stages and at most seven linear stages mounted below the focusing optics, capable of moving the focusing optics with at least one degree of freedom.

In a preferred embodiment, the gas density shaper is a device capable of changing the spatial density of the gas target, comprising at least one of the following components: a gas pressure regulator, a gas mixture regulator, and at least one wire and/or at least one sharp edge, remotely controlled and eventually automatic, that modifies the trajectory of the supersonic gas jet, thus changing the plasma density profile.

In a preferred embodiment, the gas target motors are a set of at least one linear stage capable of moving the gas target with at least one degree of freedom.

In a preferred embodiment, the radiation spectrum fine shaper comprises at least one magnetic field and at least one slit.

In a preferred embodiment, the radiation pulse particle number controller comprises at least one magnetic field and at least one slit.

In another embodiment, the radiation pulse particle number controller comprises at least one solid target and at least one slit.

In a preferred embodiment, the radiation pulse spatial distribution shaper comprises at least one solid target.

In a preferred embodiment, the radiation pulse divergence controller comprises at least one magnetic field and at least one slit.

In another embodiment, the radiation pulse divergence controller comprises at least one solid target and at least one slit.

In a preferred embodiment, radiation pulse temporal profile controller comprises at least one magnetic field.

In a preferred embodiment, radiation pulse temporal profile controller comprises at least one solid target.

In a preferred embodiment, the device is controlled by a wireless device, for example a tablet or a laptop.

The pulsed radiation source may, for example, comprise a laser master oscillator, a booster, a stretcher, a first amplifier, a laser pulse delivery system, a final amplifier, a laser transport, a laser focusing system, a plasma electron accelerator, a radiation beam delivery system.

The pulsed radiation source may comprise one radiation arm or a plurality of radiation pulse arms, such as two, three, four, five, or more radiation pulse arms. Each of the radiation pulse arms may for example comprise a final amplifier, a laser transport, a laser focusing system, a plasma electron accelerator, a radiation beam delivery system.

In a preferred embodiment, the laser master oscillator is a Ti:Sa oscillator.

In a preferred embodiment, the booster comprises a laser pulse amplifier, for example a regenerative amplifier or a multi-pass amplifier.

In a preferred embodiment of the device, the stretcher is an optical device comprising at least one pair of diffractive gratings.

In a preferred embodiment, the first amplifier and/or the final amplifier comprises a Ti:Sa crystal pumped by a diode pumped solid state laser with frequency conversion and/or a Ti:Sa crystal pumped by a flash lamp pumped solid state laser with frequency conversion.

In a preferred embodiment of the device, the laser pulse delivery system is an optical system composed by a set of fast flip mirrors. In another embodiment of the device, the laser pulse delivery system is a fast rotating mirror. In another embodiment of the device, the laser pulse delivery system comprises at least one galvo mirror.

The imaging system is synchronized with the pulsed radiation source by means of the synchronization system within a time jitter shorter than 200 ms. The imaging system can be based on various imaging technologies known to the person skilled in the art. By way of example, x-ray imaging technology, magnetic resonance imaging (MRI) technology, ballistic and snake photon technology, fluorescent markers, or Cerenkov radiation detection can be used, or a combination of any two or more of these methods.

In one embodiment, real time magnetic resonance systems capable of imaging may be used to monitor the target region with a time resolution better than 200 ms. The MRI is synchronized to the radiation pulse by the synchronization system with a time jitter lower than 200 ms.

In another embodiment, x-ray imaging system is used, wherein a synchronized x-ray source is adapted to emit x-ray for imaging in a time shorter than 200 ms. Thus, x-ray images are acquired with a time resolution better than 200 ms. The x-ray imaging system is synchronized to the radiation pulse by the synchronization system with a time jitter lower than 200 ms.

During the x-ray imaging, the additional dose deposited into the patient's body due to the imaging x-ray, depending on the part of the body and on the imaging modality, is typically in the range of 0.1-10 mSv per image, but can be lowered using special imaging techniques, as for example x-ray phase contrast imaging or x-ray fluoroscopy. This actually limits the maximum number of radiography steps that can be taken. Being capable of performing a treatment session with just few radiation pulses using the radiation source having the parameters set by the present invention provides an additional advantage over the radio frequency accelerators. The system of the present invention thus can perform x-ray imaging of the target region at each radiation pulse.

In a preferred embodiment, the x-ray imaging system comprises an electron emitter, or cathode, which may be a wire undergoing a very high current, and an anode having a potential difference with respect to the cathode of at least 20 kV.

In another embodiment, the x-ray imaging system comprises a laser system for generating laser pulses focused on a solid, liquid, gaseous or plasma target.

In a preferred embodiment, the x-ray imaging system comprises an x-ray delivery system capable of shaping the x-ray beam both in fluence and spectrum; said x-ray delivery system may be a stack of metal foils.

In one preferred embodiment, the x-ray imaging system comprises a target position diagnostics, which may be a set of digital x-ray sensors connected with the control system. The target position diagnostics is preferably adapted to perform at least one of: x-ray absorption imaging, x-ray fluoroscopy imaging, x-ray phase contrast imaging.

In another embodiment, ballistic and snake photons medical imaging technique [1] system is used, capable of acquiring images with a time resolution lower than 200 ms.

In another embodiment, an imaging system based on detecting the Cerenkov radiation emitted by the radiation beam when it enters and exits the patient's body is used. This technique is very effective since the radiation is emitted in very short time (<1 ms).

In another embodiment, imaging system based on fluorescent markers is used. Such markers can be inserted into or near the target region and can be, for example, gold particles. The role of these markers is to either appear as a strong absorption object in the radiography, or to emit characteristic radiation once irradiated by the radiation pulse. These markers help in reducing the exposure time for the target region imaging.

Optionally, the imaging technologies, in particular MRI and x-ray imaging technologies can be combined to get a more precise imaging. It is also preferable to combine any technique with fluorescent markers.

The imaging can be two-dimensional or three-dimensional.

The control system is capable of at least one of: processing the acquired x-ray image, calculating the changes to be applied to the treatment plan, and applying those changes to the x-ray machine, to the x-ray delivery system, and to the control system for the electron beam optimization.

The control system may include a control system for the electron beam optimization. The input and output of the control system for the electron beam optimization are connected with at least one component of the pulsed radiation source, for example with the laser plasma electron accelerator.

In a preferred embodiment of the device, the control system and/or the control system for the electron beam optimization is a computer.

The present invention also provides a method for testing and/or calibrating a system of the present invention, wherein a body of water (e.g., a water phantom) is irradiated by means of the pulsed radiation source by at least one pulse having the duration of less than 1 ms and depositing a dose corresponding to at least 50 mGy at a depth of at least 1 cm in water, and simultaneously the irradiated region is subjected to imaging by means of the imaging system within a time jitter shorter than 200 ms from the delivery of the irradiation pulse, wherein the imaging is carried out with a time resolution better than 200 ms, and the obtained image is used for calculating the deposited dose and optionally adjusting the system.

The present invention further provides a method for radiotherapeutics treatment of a subject in need of such treatment using the system of the present invention, wherein the subject is irradiated by means of the pulsed radiation source by at least one pulse having the duration of less than 1 ms and depositing a dose corresponding to at least 50 mGy at a depth of at least 1 cm in water, and simultaneously the subject is subjected to imaging by means of the imaging system within a time jitter shorter than 200 ms from the delivery of the irradiation pulse, wherein the imaging is carried out with a time resolution better than 200 ms, and the obtained image is used for calculating the deposited dose and optionally adjusting the treatment.

This method is advantageous over existing solutions since it allows for a precise reconstruction of the dose deposited into the target region and the patient's body. Moreover, it can be very effective in some specific cases like breast or lung tumor, where the target region is located in a fast moving region of the patient's body. In such cases this method helps in understanding how well the tumor was hit by the radiation pulse, and which fraction of the radiation has been delivered to the healthy tissue of the patient.

In a preferred embodiment, the imaging system comprises at least one pulsed x-ray imaging system and/or at least one MRI imaging unit.

In a preferred embodiment, the imaging system can monitor the target region via time-resolved 2-D or 3-D images.

In a preferred embodiment, gated radiotherapy technique is used for irradiation.

In a preferred embodiment, the imaging used is Cerenkov imaging to detect the in and out position of the radiation beam.

In a preferred embodiment, this method further comprises that after each radiation pulse, after few radiation pulses, or after the whole treatment session, the target region images are analyzed and the information about the position and, eventually, the shape of the target region are used in combination with the data relative to the radiation pulses to improve the treatment plan.

BRIEF DESCRIPTION OF DRAWINGS

FIG. 1 schematically illustrates one embodiment of the components of the device.

FIG. 2 schematically illustrates two different configuration embodiments for the laser transport.

FIG. 3 schematically illustrates one embodiment of the workflow of the control system of the device.

FIG. 4 schematically illustrates one embodiment of the pulsed radiation source, in the case of multiple radiation pulse arms, in particular with three radiation pulse arms.

FIG. 5 schematically illustrates one embodiment of the system with multiple radiation pulse arms mounted on robotic arms and multiple x-ray imaging modules mounted on static support, in particular with two radiation pulse arms and two x-ray imaging modules.

FIG. 6 schematically illustrates one embodiment of the system with MRI imaging system, x-ray imaging system and two radiation pulse arms, in particular with one radiation pulse arm implemented in the MRI imaging system.

FIG. 7 shows a 2-D plot of the dose deposited inside a 10×20 cm water phantom by one of the possible beams emitted by the pulsed radiation source.

DESCRIPTION OF EMBODIMENTS

Details of the present invention are further illustrated using the following exemplary embodiments. However, these examples should not be construed as limiting the scope of the claimed invention. Unless indicated otherwise, the embodiments shown in the figures are independent and may be used separately or in combination.

FIG. 1 schematically represents one possible embodiment of the system, in this specific case using x-ray imaging and a laser plasma electron accelerator. The synchronization system 101 synchronizes, with a time jitter lower than 200 ms, the emission of an x-ray pulse from the x-ray machine 107 and the emission of a laser pulse from the laser system 102. The laser pulse is transported through the laser transport 103, and then focused by the laser focusing system 104 into the plasma electron accelerator 105. Each single electron beam generated in the plasma electron accelerator 105 goes into the radiation beam delivery system 106, which operates on each electron pulse and sends to the target 110 a radiation pulse. The radiation beam delivery system 106 can check the electron beam quality and can stop or modify the beam in order to meet the requirements set by the treatment plan. The radiation beam delivery system 106 may also use the kinetic energy of the electron beam to create a different particle beam, for example a beam of high energy photons, positrons, neutrons or pi mesons. For this reason, the radiation pulse sent to the target by the radiation beam delivery system 106 is not restricted to be an electron beam, but could also be, for example, a high energy photon beam, a positron beam, a neutron beam, a pi meson beam, or a beam containing a mixture of these particles. While the radiation pulse hits the target 110, the x-ray pulse coming from the x-ray machine 107, and shaped by the x-ray delivery system 108, hits the target 110 within a time window shorter than 200 ms. The target position diagnostics 109 detect the x-ray signal coming from the x-ray delivery system 108, after it passes through the target 110.

In a preferred embodiment, the synchronization system 101 is an electrical device capable of sending electrical pulses synchronized with a tunable delay with a time resolution better than 200 ms.

In a preferred embodiment, the laser system 102 is a Ti:Sa laser, delivering laser pulses with energy of at least 100 mJ and pulse duration shorter than 1 µs.

In another embodiment, the laser system 102 is a Ti:Sa laser, pumped by diode pumped solid state lasers with frequency conversion, delivering laser pulses with energy of at least 100 mJ and pulse duration shorter than 1 µs.

In a preferred embodiment, as schematically illustrated in FIG. 2 (a), the laser transport 103 comprises the compressor 202, which compresses the laser pulse in time to less than 100 fs, and the transport 203, which is an optical transport line that sends the laser pulse to the laser focusing system 104.

In another embodiment, as schematically illustrated in FIG. 2 (b), the laser transport 103 comprises a phased optical fiber array 201, which transports the uncompressed laser pulse, which has time duration of at least 10 ps, to the compressor 202. The compressor 202 compresses the laser pulse in time to less than 100 fs and then it sends the laser pulse to the transport 203, which is an optical transport line that sends the laser pulse to the laser focusing system 104.

In a preferred embodiment, the laser focusing system 104 is an optical system that focuses the laser pulse inside the plasma electron accelerator 105, comprising at least one positioning mirror and at least one off-axis parabola capable of focusing the laser pulse to intensity higher than $10^{12}$ W/cm$^2$.

In a preferred embodiment, the laser focusing system 104 is an optical system that focuses the laser pulse inside the plasma electron accelerator 105, comprising at least one positioning mirror and at least one spherical mirror capable of focusing the laser pulse to intensity higher than $10^{12}$ W/cm$^2$.

In a preferred embodiment, the plasma electron accelerator 105 is a device comprising at least one gas target mounted on a remotely controlled motorized stage with at least one degree of freedom to align the gas target according to the laser focus.

In a preferred embodiment, the radiation beam delivery system 106 is a device comprising at least one of the following components: a magnetic field to select the energy of the electron beam and to eventually shape the electron beam, a beam charge diagnostic, a magnetic system to change the size of the electron beam, and eventually focus or defocus it, and a solid target to change the beam divergence and/or to generate other particle beams, for example high energy photons (x-ray and gamma-ray), positrons, neutrons or pi mesons.

In a preferred embodiment, the x-ray machine 107 is a device comprising an electron emitter, or cathode, which may be a wire undergoing a current higher than 1 µA, and an anode having a potential difference with respect to the cathode of at least 20 kV.

In another embodiment, the x-ray machine 107 is a device comprising laser pulses that can come from the laser system 102 or from an independent laser system, focused on a solid, liquid, gaseous or plasma target.

In a preferred embodiment, the x-ray delivery system 108, is a device capable of shaping the x-ray beam fluence and/or spectrum, which may be a stack of metal foils.

In a preferred embodiment, the target position diagnostics 109 may be a set of digital x-ray sensors connected with the control system 301. The control system 301 is capable of doing, at each irradiation step, at least one of the following: processing the acquired x-ray image, calculating the changes to be applied to the treatment plan, and applying those changes to the x-ray machine 107, to the x-ray delivery system 108, and to the control system for the electron beam optimization 306.

In a preferred embodiment, the target position diagnostics 109 can be set to perform x-ray absorption imaging, x-ray fluoroscopy imaging or x-ray phase contrast imaging.

The system may contain a control system for the electron beam optimization 306. In the following, the input and output of the control system for the electron beam optimization 306 are connected with some sub-parts of the laser plasma electron accelerator, but they can be connected to different sub-parts of the laser plasma electron accelerator, as well known to those skilled in the art.

Each laser pulse, originated in the laser system 102, and passing through the laser transport 103, the laser focusing system 104 and the plasma electron accelerator 105, can be monitored by several diagnostics. Among these diagnostics there is at least one of the following: the spectral shape diagnostic, which measures the spectral shape of the laser pulse; the energy diagnostic, which measures the energy of the laser pulse; the beam shape diagnostic, which measures the energy distribution of the laser pulse along its transverse section; the spectral phase diagnostic, which measures the spectral phase of the laser pulse; the temporal profile diagnostic, which measures the temporal profile of the laser pulse; the laser focal spot diagnostic, which measures the spatial distribution of the laser pulse in its focus; and the wavefront diagnostic, which measures the phase front of the laser pulse. The gas target that emits the electron pulses can be monitored by several diagnostics. Among these diagnostics there is at least one of the following: the plasma diagnostic, which measures the plasma density inside the target; the laser plasma coupling diagnostic, which measures the coupling in the laser plasma interaction; and the laser propagation diagnostic, which measures the laser propagation after the plasma. The electron pulses accelerated by the plasma electron accelerator 105 can be monitored by several diagnostics. Among these diagnostics, there is at least one of the following: the electron beam shape diagnostic, which measures the transverse shape of the electron pulse; the electron beam charge diagnostic, which measures the charge of the electron pulse; the electron beam spectral shape diagnostic, which measures the spectral shape of the electron pulse; the beam divergence diagnostic, which measures the divergence of the electron pulse; and the beam temporal profile diagnostic, which measures the temporal profile of the electron pulse. The data acquired by the diagnostics are sent to the control system for the electron beam optimization 306, which analyzes them and, eventually, saves the results. In the case the electron beam is not satisfying the parameters required for the treatment, the control system for the electron beam optimization 306 modifies the state of some components until the electron beam reaches the parameters desired. The control system for the electron beam optimization 306 operates on at least one of the following components: the spectral shaping device, to modify the spectral shape of the laser pulses; the energy attenuator, to change the energy of the laser pulses; the spectral phase shaper, to modify the spectral phase of the laser pulses; the compressor gratings motors, to change the duration and/or the temporal profile of the laser pulses; the positioning motors, to modify the path of the laser pulses in the laser focusing system 104; the focusing optics motors, to modify the position and the shape of the laser focal spot; the gas density shaper, to modify the density profile of the gas target; the gas target motors, to change the position of the gas target within the plasma electron accelerator 105; the adaptive optics, to modify the wavefront of the laser pulse, and so the shape of the focal spot; the radiation spectrum fine shaper, which modifies the spectrum of the radiation pulse; the radiation pulse particle number controller, which adjusts the number of particles in the radiation pulse; the radiation pulse spatial distribution shaper, which modifies the spatial distribution of the radiation pulse; the radiation pulse divergence controller, which adjusts the divergence of the radiation pulse; and the radiation pulse temporal profile controller, which adjusts the duration and/or the temporal profile of the radiation pulse.

In a preferred embodiment, the control system for the electron beam optimization 306 is a computer.

In a preferred embodiment, the spectral shape diagnostic can be an optical and infrared light spectrometer.

In a preferred embodiment, the spectral shaping device is a mazzler.

In another embodiment, the spectral shaping device comprises at least one colored optical filter.

In another embodiment, the spectral shaping device comprises at least one prism and at least one neutral optical filter.

In a preferred embodiment, the energy diagnostic is a calorimeter.

In another embodiment, the energy diagnostic comprises at least one optical diode.

In a preferred embodiment, the energy attenuator comprises at least one half-lambda plate and at least one polarizer.

In a preferred embodiment, the beam shape diagnostics comprises a set of mask filters.

In another embodiment, the beam shape diagnostics comprises a camera and imaging optics.

In a preferred embodiment, the spectral phase diagnostic comprises at least one of the following devices: SPIDER, FROG, D-SCAN and GRENOUILLE.

In a preferred embodiment, the spectral phase shaper is a dazzler.

In a preferred embodiment, the adaptive optics comprise a deformable mirror.

In a preferred embodiment, the temporal profile diagnostic comprises at least one of the following devices: SPIDER, FROG, D-SCAN and GRENOUILLE.

In a preferred embodiment, the compressor gratings motors comprise at least one linear stage mounted below one of the gratings to change the optical path of different wavelengths.

In another embodiment, the compressor grating motors comprise at least one rotative stage mounted below one of the gratings to change the optical path of different wavelengths.

In a preferred embodiment, the positioning motors comprise at least one actuator mounted on at least one mirror mount capable of moving with at least one degree of freedom the at least one positioning mirror.

In a preferred embodiment, the focusing optics motors comprise at most five rotation stages and at most seven linear stages mounted below the focusing optics, capable of moving the focusing optics with at least one degree of freedom.

In a preferred embodiment, the electron beam shape diagnostic comprises at least one fluorescent screen coupled with a CCD.

In a preferred embodiment, the electron beam charge diagnostic comprises at least one Integrating Current Transformer.

In another embodiment, the electron beam charge diagnostic comprises at least one fluorescent screen coupled with a CCD.

In a preferred embodiment, the electron beam spectral shape diagnostic is a device which comprises at least one magnetic dipole and at least one fluorescent screen coupled with a CCD.

In a preferred embodiment, the laser focal spot diagnostic comprises a CCD and a reflective object.

In a preferred embodiment, the plasma diagnostic comprises at least one CCD with imaging optics looking at the gas target.

In a preferred embodiment, the gas density shaper is a device capable of changing the spatial density of the gas target, comprising at least one of the following components: a gas pressure regulator, a gas mixture regulator, and at least one wire and/or at least one sharp edge, remotely controlled and eventually automatic, that modifies the trajectory of the supersonic gas jet, thus changing the plasma density profile.

In a preferred embodiment, the gas target motors are a set of at least one linear stage capable of moving the gas target with at least one degree of freedom.

In a preferred embodiment, the wavefront diagnostic comprises a wavefront sensor.

In a preferred embodiment, the laser propagation diagnostic comprises a CCD looking at the laser exiting the target.

In a preferred embodiment, the laser plasma coupling diagnostic comprises a CCD with imaging optics looking at the light emitted by the target.

In a preferred embodiment, the beam divergence diagnostic comprises at least one fluorescent screen coupled with a CCD.

In a preferred embodiment, the beam temporal profile diagnostic comprises a streak camera with a resolution better than 10 ps.

In another embodiment, the beam temporal profile diagnostic comprises an infrared spectrometer and a metallic target.

In a preferred embodiment, the radiation spectrum fine shaper comprises at least one magnetic field and at least one slit.

In a preferred embodiment, the radiation pulse particle number controller comprises at least one magnetic field and at least one slit.

In another embodiment, the radiation pulse particle number controller comprises at least one solid target and at least one slit.

In a preferred embodiment, the radiation pulse spatial distribution shaper comprises at least one solid target.

In a preferred embodiment, the radiation pulse divergence controller comprises at least one magnetic field and at least one slit.

In another embodiment, the radiation pulse divergence controller comprises at least one solid target. In a preferred embodiment, the radiation pulse temporal profile controller comprises at least one magnetic field.

In another embodiment, the radiation pulse temporal profile controller comprises at least one solid target.

In a preferred embodiment, the device is controlled by a wireless device, for example a tablet or a laptop.

FIG. 3 schematically illustrates one embodiment of the control system of the device, in the case of a laser plasma electron accelerator as a pulsed radiation source and a generic imaging system. The control system 301 receives from the imaging system 302 the data containing information on the position and, eventually, the shape of the target region. The control system 301 elaborates the data received and creates a geometry reconstruction 303 to locate the target region in a 2D or 3D coordinate system. If the data coming from the imaging system 302 are not accurate enough for the geometry reconstruction, the control system 301 can operate on the imaging system 302 in order to get more accurate imaging data. Then, using the data concerning the radiation pulse coming from at least one among the radiation beam delivery system 106, the plasma electron accelerator 105, and the control system for the electron beam optimization 306; the control system 301 creates a map of the dose deposited into the patient's body and into the target region 304 using the same 2D or 3D coordinate system. After, the control system 301 compares the map of the dose deposited into the patient's body and into the target region 304 with the predicted dose deposited map, and eventually creates a modified treatment plan 305. After, the control system 301 operates on the control system for the electron beam optimization 306 and/or on the radiation beam delivery system 106, to meet the requirements for the subsequent radiation pulse to be delivered according to the current treatment plan.

FIG. 4 schematically illustrates one possible embodiment of the pulsed radiation source, in the case of multiple radiation pulse arms, in particular with three radiation pulse arms. In this case, each of the three arms is a laser plasma electron accelerator.

The laser master oscillator 401 sends fs, nJ pulses at a MHz repetition rate to the booster 402, where the energy is increased at least to the µJ level and the repetition rate lowered to the kHz level. Then the laser pulses are sent to the stretcher 403, where they are elongated in time to at least 10 ps. After they are sent to the first amplifier 404, which delivers laser pulses at a frequency of at least 5 Hz and with an energy of at least few mJ to the laser pulse delivery system 405. The laser pulse delivery system 405 can either stop the laser pulses or deliver each of them to the first radiation pulse arm 421, or to the second radiation pulse arm 422, or to the third radiation pulse arm 423. All the radiation pulse arms in this scheme are equivalent. The final amplifier 406, 407, 408 receives the laser pulses coming from the laser pulse delivery system 405, amplifies them to at least 100 mJ and then sends them to the laser transport 409, 410, 411. The laser transport 409, 410, 411 compresses the laser pulses in time into the 20-200 fs range and sends them to the laser focusing system 412, 413, 414, which focuses the laser pulses into the plasma electron accelerator 415, 416, 417. The plasma electron accelerator 415, 416, 417 uses the laser pulses to accelerate the electron pulses, and sends these last to the radiation beam delivery system 418, 419, 420, where each radiation pulse can be controlled, modified and eventually blocked.

In the following, at least one possible realization of each component disclosed in FIG. 4 is disclosed.

In a preferred embodiment, the laser master oscillator 401 is a Ti:Sa oscillator.

In a preferred embodiment, the booster 402 comprises a laser pulse amplifier, for example a regenerative amplifier or a multi-pass amplifier.

In a preferred embodiment, the stretcher 403 is an optical device comprising at least one pair of diffractive gratings.

In a preferred embodiment, the $1^{st}$ amplifier 404 comprises a Ti:Sa crystal pumped by a diode pumped solid state laser with frequency conversion.

In another embodiment, the $1^{st}$ amplifier 404 comprises a Ti:Sa crystal pumped by a flash lamp pumped solid state laser with frequency conversion.

In a preferred embodiment, the laser pulse delivery system 405 is an optical system composed by a set of fast flip mirrors.

In another embodiment, the laser pulse delivery system 405 is a fast rotating mirror.

In another embodiment, the laser pulse delivery system 405 comprises at least one galvo mirror.

In a preferred embodiment, the final amplifiers 406, 407 and 408 comprise Ti:Sa crystals pumped by diode pumped solid state lasers with frequency conversion.

In a another embodiment, the final amplifiers 406, 407 and 408 comprise Ti:Sa crystals pumped by flash lamp pumped solid state laser with frequency conversion.

FIG. 5 schematically illustrates one exemplary embodiment of the system with multiple radiation pulse arms mounted on robotic arms and multiple imaging modules mounted on static supports, in particular with two laser plasma electron accelerators and two x-ray imaging modules. The laser pulse delivery system located on the common laser table 501 sends selectively the laser pulses to the final amplifier tables 502 or 503. The amplified laser pulses are then sent to the radiation stations 504 or 505. The radiation stations send their radiation pulses to the patient lying on the treatment bed 509; at the same time the x-ray sources 506 and 507, triggered by the synchronization system, irradiate the target region. The x-ray detector 508 and another x-ray sensor located inside the treatment bed 509 collect the attenuated x-ray and send these data to the control system 301.

In a preferred embodiment of the device, the common laser table 501 comprises at least one laser master oscillator, at least one booster, at least one stretcher, at least one first amplifier, and at least one laser pulse delivery system.

In a preferred embodiment of the device, the radiation stations 504 and 505 are devices fixed to the ground, to a wall or to the ceiling of the treatment room.

In a preferred embodiment, each of the radiation stations 504 and 505 comprises a laser transport, a laser focusing system, a plasma electron accelerator, and a radiation beam delivery system.

In a preferred embodiment, at least one of the radiation stations 504 and 505 comprises a laser transport comprising a phased optical fiber array.

In a preferred embodiment, at least one of the radiation stations 504 and 505 comprises a robotic arm or a gantry capable of moving the plasma electron accelerator.

In another embodiment, at least one of the radiation stations 504 and 505 comprises a robotic arm or a gantry capable of moving the radiation beam delivery system.

In another embodiment, at least one of the radiation stations 504 and 505 comprises a robotic arm or a gantry capable of moving both the plasma electron accelerator and the radiation beam delivery system.

In another embodiment, at least one of the radiation stations 504 and 505 comprises a robotic arm or a gantry capable of moving the compressor, the transport, the laser focusing system, the plasma electron accelerator and the radiation beam delivery system.

In a preferred embodiment of the device, the x-ray sources 506 and 507 are devices comprising at least one x-ray machine and at least one x-ray delivery system.

In a preferred embodiment of the device, at least one of the x-ray sources 506 and 507 comprises a robotic arm or a gantry capable of moving at least one x-ray machine and at least one x-ray delivery system.

In a preferred embodiment of the device, the x-ray detector 508 comprises at least one fluorescent screen coupled with a CCD.

In another embodiment of the device, the x-ray detector 508 comprises at least one digital x-ray detector.

In a preferred embodiment of the device, the treatment bed 509 is a stable bed movable along at least one direction.

In a preferred embodiment of the device, the treatment bed 509 has an x-ray detector 508 integrated.

FIG. 6 schematically illustrates an exemplary embodiment of the device with a combination of different imaging systems and multiple radiation pulse arms; in particular with one MRI imaging system, one x-ray imaging system, and two radiation pulse arms. The radiation pulse arm 602 is implemented into the MRI imaging system 601. The radiation pulse arm 603 is stand-alone and pointing toward the patient, that is laying on the treatment bed 604. The x-ray source 605 is pointed toward the patient and the x-ray detector 606 collects the x-ray passing through the patient.

In a preferred embodiment, the MRI imaging system 601 is capable of imaging the target region with a time resolution better than 200 ms.

In a preferred embodiment, the radiation pulse arm implemented into the MRI 602 is a laser plasma electron accelerator emitting neutral radiation.

In a preferred embodiment, the radiation pulse arm 603 can be mounted on a static support, on a mechanically movable support, on a robotic arm, or on a gantry.

In a preferred embodiment of the device, the MRI imaging system 601, the radiation pulse arm 602, the radiation pulse arm 603 and the x-ray imaging system 605 are synchronized by a common synchronization system with a time resolution better than 200 ms.

In a preferred embodiment of the device, the treatment bed 604 may have an x-ray sensor incorporated.

In another embodiment of the device, the treatment bed 604 can move along at least one direction.

In a preferred embodiment of the device, the x-ray detector 606 can be set to perform x-ray absorption imaging, x-ray fluoroscopy imaging or x-ray phase contrast imaging.

FIG. 7 shows a 2-D plot describing the dose deposited inside a 10×20 cm water phantom by one of the possible beams emitted by the pulsed radiation source described in this patent application. In particular, it shows a beam containing 80 pC of electrons with 100 MeV kinetic energy. As it can be observed, a single radiation pulse of this kind can deposit a dose higher than 50 mGy at a depth of at least 1 cm in water.

CITATION LIST

[1] S. Farsiu et al., "Statistical detection and imaging of objects hidden in turbid media using ballistic photons", Applied Optics, Vol. 46 No. 23 (2007).

The invention claimed is:

1. A method for testing and/or calibrating a system for radiotherapy, wherein a body of water is irradiated by means of a pulsed radiation source by at least one pulse having duration of less than 1 ms and depositing a dose corresponding to at least 50 mGy at a depth of at least 1 cm in water, and simultaneously an irradiated region is subjected to imaging by means of an imaging system within a time jitter shorter than 200 ms from delivery of an irradiation pulse, wherein the imaging is carried out with a time resolution shorter than 200 ms, and an obtained image is used for calculating the deposited dose.

2. A system for radiotherapy which comprises at least one pulsed radiation source for delivering radiation pulses shorter than 1 ms, at least one imaging system, at least one control system for determining a deposited dose, and at least one synchronization system for synchronizing said pulsed radiation source and said imaging system within a time jitter shorter than 200 ms, wherein said pulsed radiation source is capable of delivering a dose of at least 50 mGy at a depth of at least 1 cm in water within 1 ms, wherein said imaging system has a time resolution shorter than 200 ms, and wherein said control system is connected to the pulsed radiation source and to the imaging system.

3. The system according to claim 2, wherein the pulsed radiation source is selected from the group comprising: sources of electron beams, sources of high energy photon beams (x-ray or gamma-ray), sources of positron beams, sources of neutron beams, sources of pi meson beams, sources of beams comprising combinations of these particles.

4. The system according to claim 2, wherein the pulsed radiation source comprises a device selected from the group: a ultra-fast laser system, a laser transport system, a laser focusing system, a laser plasma electron accelerator, a radiation beam delivery system.

5. The system according to claim 4, wherein the ultra-fast laser system is a Ti:Sa laser system, a diode pumped solid state laser system (DPSSL) or a phased optical fiber array laser system; said ultra-fast laser system being pumped by a diode laser, by a diode pumped solid state laser with frequency conversion, by a flash lamp pumped solid state laser with frequency conversion, or by a combination of these systems.

6. The system according to claim 2, wherein the control system is capable, after each irradiation step of at least one of the following: processing an acquired image, calculating changes to be applied to a treatment plan, operating on the imaging system, and operating on the pulsed radiation source.

7. The system according to claim 2, wherein the pulsed radiation source comprises at least one laser beam diagnostic, selected from: a spectral shape diagnostic for measuring a spectral shape of a laser pulse; an energy diagnostic for measuring energy of the laser pulse; a beam shape diagnostic for measuring energy distribution of the laser pulse along its transverse section; a spectral phase diagnostic for measuring a spectral phase of the laser pulse; a temporal profile diagnostic for measuring a temporal profile of the laser pulse; a laser focal spot diagnostic for measuring a spatial distribution of the laser pulse in its focus; and a wavefront diagnostic for measuring a phase front of the laser pulse.

8. The system according to claim 2, wherein the pulsed radiation source comprises a gas target for emitting electron pulses monitored by one or more diagnostics selected from: a plasma diagnostic for measuring plasma density inside a target; a laser plasma coupling diagnostic for measuring coupling in laser plasma interaction; and a laser propagation diagnostic for measuring laser propagation after the plasma.

9. The system according to claim 2, wherein the pulsed radiation source comprises one or more diagnostics selected from: an electron beam shape diagnostic for measuring a transverse shape of an electron pulse; a beam charge diagnostic for measuring a charge of the electron pulse; an electron beam spectral shape diagnostic for measuring a spectral shape of the electron pulse; a beam divergence diagnostic for measuring divergence of the electron pulse; and a beam temporal profile diagnostic for measuring a temporal profile of the electron pulse.

10. The system according to claim 2, wherein the pulsed radiation source comprises a control system for electron beam optimization for collecting data from all diagnostics, analyzing said data, modifying a state of one or more components of the pulsed radiation source, and saving results.

11. The system according to claim 2, wherein the pulsed radiation source comprises at least one of the following components: a spectral shaping device for modifying a spectral shape of a laser pulse; an energy attenuator for changing energy of the laser pulse; a spectral phase shaper for modifying a spectral phase of the laser pulse; compressor gratings motors for changing a duration and/or a temporal profile of the laser pulse; positioning motors for modifying a path of the laser pulse in a laser focusing system; focusing optics motors for modifying a position and shape of laser focal spot; a gas density shaper for modifying a density profile of gas target; gas target motors for changing a position of the gas target within a plasma electron accelerator; adaptive optics for modifying a wavefront of the laser pulse and so the shape of a focal spot; a radiation spectrum fine shaper for modifying a spectrum of a radiation pulse; a radiation pulse particle number controller for adjusting a number of particles in the radiation pulse; a radiation pulse spatial distribution shaper for modifying a spatial distribution of the radiation pulse; a radiation pulse divergence controller for adjusting divergence of the radiation pulse; and a radiation pulse temporal profile controller for adjusting temporal profile of the radiation pulse.

12. The system according to claim 2, wherein the pulsed radiation source comprises a laser master oscillator, a booster, a stretcher, a first amplifier, a laser pulse delivery system, and one or more pulsed radiation arms; wherein each said pulsed radiation arm comprises a final amplifier, a laser transport system, a laser focusing system, a laser plasma electron accelerator, a radiation beam delivery system.

13. The system according to claim 2, wherein the imaging system is based on pulsed x-ray imaging technology, or magnetic resonance imaging (MRI) technology, or ballistic and snake photon technology, or fluorescent markers, or Cerenkov radiation detection, or a combination of any two or more of these technologies.

14. The system according to claim 2, wherein the imaging system comprises at least one of the following: a laser system pointing on a target region and a gated detector, a real time magnetic imaging device; a laser system and at least one laser delivery system capable of focusing laser pulses at an intensity higher than $10^{10}$ W/cm$^2$ on a solid, liquid gaseous or plasma target, a device comprising an electron emitter, or cathode, being a wire undergoing a current higher than 1 µA, an anode having a potential difference with respect to the cathode of at least 20 kV, a x-ray delivery system and a x-ray detector; a x-ray source capable of performing x-ray phase contrast imaging.

15. The system according to claim 2, wherein the synchronization system comprises at least one ultra-fast laser system shared with the imaging system and with the pulsed radiation source.

16. The system according to claim 2, comprising a control system for electron beam optimization, wherein input and output of said control system for the electron beam optimization are connected with at least one component of the pulsed radiation source, said at least one component is a laser plasma electron accelerator.

17. The system according to claim 2, wherein at least one pulsed radiation source and/or at least one imaging system, is mounted on a static or a movable support, and wherein the static or the movable support is a gantry or a robotic arm.

18. The system according to claim 2, wherein a laser transport system comprises a phased optical fiber array that brings uncompressed laser pulses from a last laser amplifier to a compressor.

19. A method for radiotherapeutic treatment of a subject in need of such treatment using the system of claim 2, wherein the subject is irradiated by means of the pulsed radiation source by at least one pulse having a duration of less than 1 ms and depositing a dose corresponding to at least 50 mGy at a depth of at least 1 cm in water, and simultaneously the subject is subjected to imaging by means of the imaging system within a time jitter shorter than 200 ms from the delivery of an irradiation pulse, wherein the imaging is carried out with a time resolution shorter than 200 ms, and an obtained image is used for calculating the deposited dose.

20. The method according to claim 19, which further comprises that after each radiation pulse, after radiation pulses, or after a whole treatment session, target region images are analyzed and information on a position and, eventually, a shape of a target region are used, in combination with data relative to radiation pulses, to calculate a dose deposited into the target region and into healthy tissue, and to improve a treatment plan.

* * * * *